(12) United States Patent
Hofmann

(10) Patent No.: US 6,217,577 B1
(45) Date of Patent: Apr. 17, 2001

(54) OUTER FIXING DEVICE FOR ORTHOPEDICS AND TRAUMATOLOGY

(75) Inventor: Roberto Maria Hofmann, Biassono (IT)

(73) Assignee: Medicalplastic S.r.L., Milan (IT)

( * ) Notice: Subject to any disclaimer, the term of this patent is extended or adjusted under 35 U.S.C. 154(b) by 0 days.

(21) Appl. No.: 09/489,029

(22) Filed: Jan. 21, 2000

(30) Foreign Application Priority Data

Jan. 21, 1999 (IT) .............................................. MI99A0100

(51) Int. Cl.[7] .................................................. A61B 17/60
(52) U.S. Cl. ................................................. 606/57; 606/54
(58) Field of Search ................................. 606/57, 54, 63

(56) References Cited

U.S. PATENT DOCUMENTS

| | | | | |
|---|---|---|---|---|
| 2,250,417 | * | 7/1941 | Ettinger | 606/54 |
| 4,848,368 | * | 7/1989 | Kronner | 606/57 |
| 5,019,077 | * | 5/1991 | De Bastiani et al. | 606/57 |
| 5,160,335 | * | 11/1992 | Wagenknecht | 606/57 |
| 5,601,551 | * | 2/1997 | Taylor et al. | 606/57 |
| 5,788,695 | * | 8/1998 | Richardson | 606/57 |
| 5,827,282 | * | 10/1998 | Pennig | 606/57 |
| 6,001,097 | * | 12/1999 | Campopiano et al. | 606/54 |

\* cited by examiner

*Primary Examiner*—Paul J. Hirsch
(74) *Attorney, Agent, or Firm*—Browdy and Neimark

(57) ABSTRACT

There is disclosed a fixing device comprising: a bar (4), at least one turret-like support (8a) having an outer casing (9) movably mounted on said bar (4), an articulated joint (12) for supporting surgical elements (2), placed at an end of the turret-like support (8a) and angularly movable relative to the outer casing (9), a single locking device (15) being provided for securing the outer casing (9) to the bar (4) and locking the angular position of the articulated joint (12), which device comprises a cam (17) movably supported by the outer casing (9) and placed between the bar (4) and the articulated joint (12) and having a forcing position at which the bar (4) and the articulated joint (12) are both locked by pressing, a single drive member (16) being also provided for operating the cam (17).

12 Claims, 5 Drawing Sheets

OUTER FIXING DEVICE FOR ORTHOPEDICS AND TRAUMATOLOGY

FIELD OF THE INVENTION

The invention relates to an outer fixing device for orthopedics and traumatology, in particular of a single-sided structure, for fixation of bone fractures.

DESCRIPTION OF THE PRIOR ART

It is known that several different outer fixing devices presently exist in the orthopedic and traumatological field for use in locking bone fragments to their correct position to enable callus formation.

Said fixing devices are apparatuses comprising a preferably tubular and telescopic bar and at least one turret-like support, also merely called turret due to its shape, emerging from the bar.

Usually two turrets are provided at least one of which is freely movable and can be freely positioned.

Turrets, by appropriate articulated joints and couplings, support surgical elements such as long and special surgical screws for example, that can be inserted by screwing into bone fragments to be held in a steady position.

Features that these apparatuses must possess are not only reliability and solidity, since any yielding or structural movement altering the established position is not admissible, but also versatility and simplicity in application.

Versatility is connected with the fact that apparatuses must adapt themselves to the most different situations, in particular because said surgical screws or in general said surgical elements must be arranged in all required directions and positions.

For the purpose, turrets must be made freely movable with respect to each other and to the telescopic bar and in addition said screws must be allowed to take various inclinations relative to the turrets supporting them.

Simplicity in application or use is important in order to avoid mounting errors and reduce operation times to a minimum in the operating theatre or the first aid station.

Reconciling these different requirements is in many instances difficult and it is pointed out in this connection that known outer fixing devices have some drawbacks.

In fact, in order to provide said turrets and surgical screws with various freedom degrees or movement and positioning directions, different technical solutions have been set up which are quite complicated and require difficult application operations.

In particular, the required time for steadily locking both turrets and said surgical elements is relatively high.

In fact it is necessary to intervene at many articulation points and tighten appropriate locking members, such. as nuts, screw heads or bolts, for example.

In this way not only time and skill are required, since all points are not in a convenient access position, but, in addition, locking of some pieces may be forgotten or intervention may not be constant and reliable at all points, which greatly affects steadiness of the outer fixing devices.

SUMMARY OF THE INVENTION

Under this situation, the technical task of the invention is to provide a fixing device capable of obviating the above drawbacks.

Within the scope of this technical task it is an important aim of the invention to provide a fixing device that, while being of ready locking, has full movement and positioning possibilities as regards turrets and surgical elements.

It is a further aim of the invention to provide a fixing device which is simple and also reliable and of reduced weight.

The aims specified are achieved by an outer fixing device for orthopedics and traumatology comprising: a bar defining a longitudinal axis, at least one turret-like support having an outer casing movably mounted on said bar, engagement means and relative drive means for fastening said outer casing to said bar, at least one articulated joint for supporting surgical elements, connected to said turret-like support and angularly movable relative to said outer casing, and engagement means and relative drive means for locking the angular position of said articulated joint, in order to secure said outer casing to said bar and lock the angular position of said articulated joint a single locking device being provided which comprises at least one cam movably supported by said outer casing and placed between said bar and said articulated joint and showing a forcing position at which said bar and said articulated joint are both locked by pressing and a single drive member active on said cam being provided for operating said locking device.

BRIEF DESCRIPTION OF THE DRAWINGS

Description of a fixing device in accordance with the invention is now given by way of non-limiting example, with reference to the drawings, in which.

DESCRIPTION OF THE PREFERRED EMBODIMENT

Figure 1:
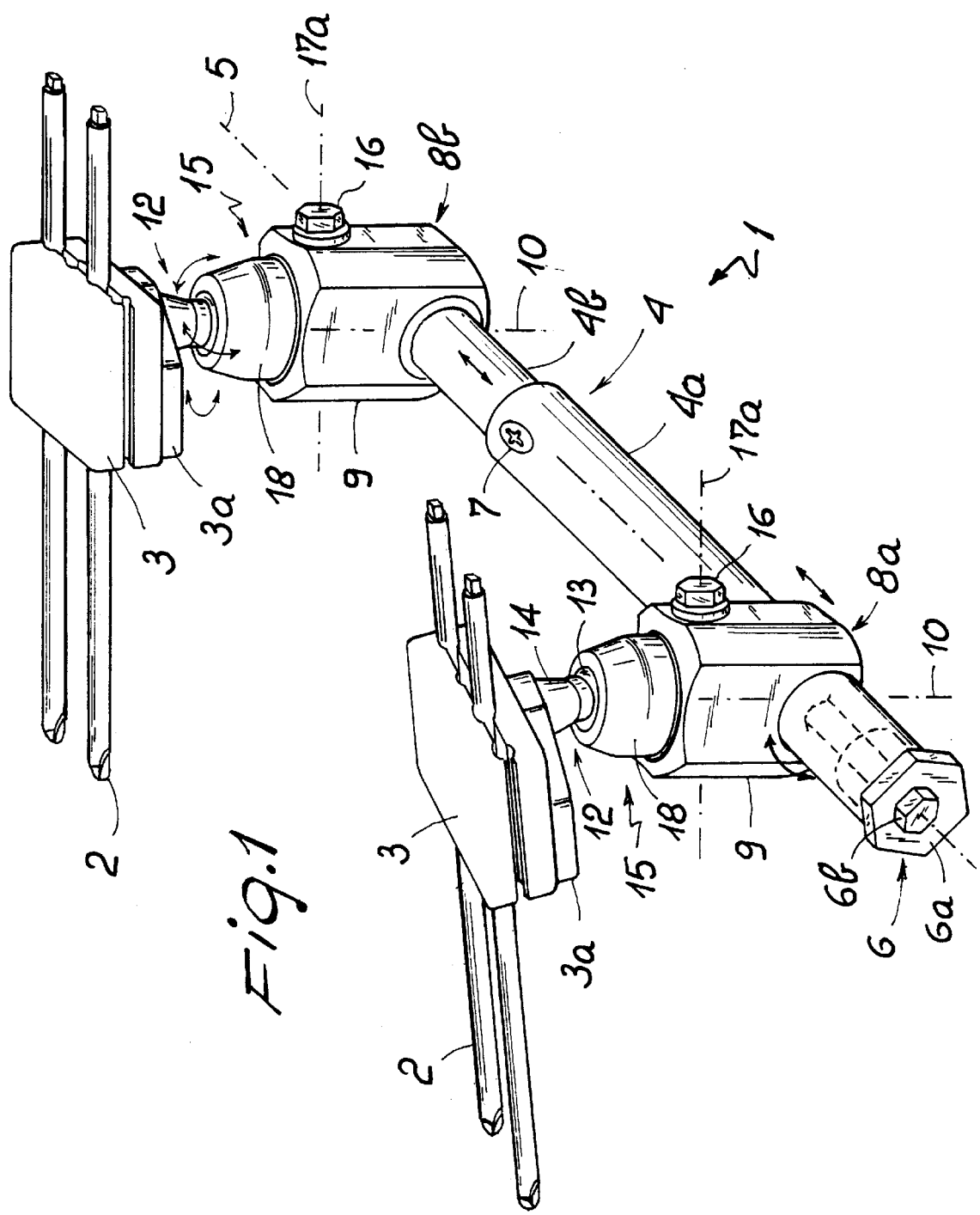
FIG. 1 is a perspective view of a fixing device of the single-sided type, taken as a whole, for fixation of bone fractures by surgical screws mounted on turret-like supports.
Figure 2:
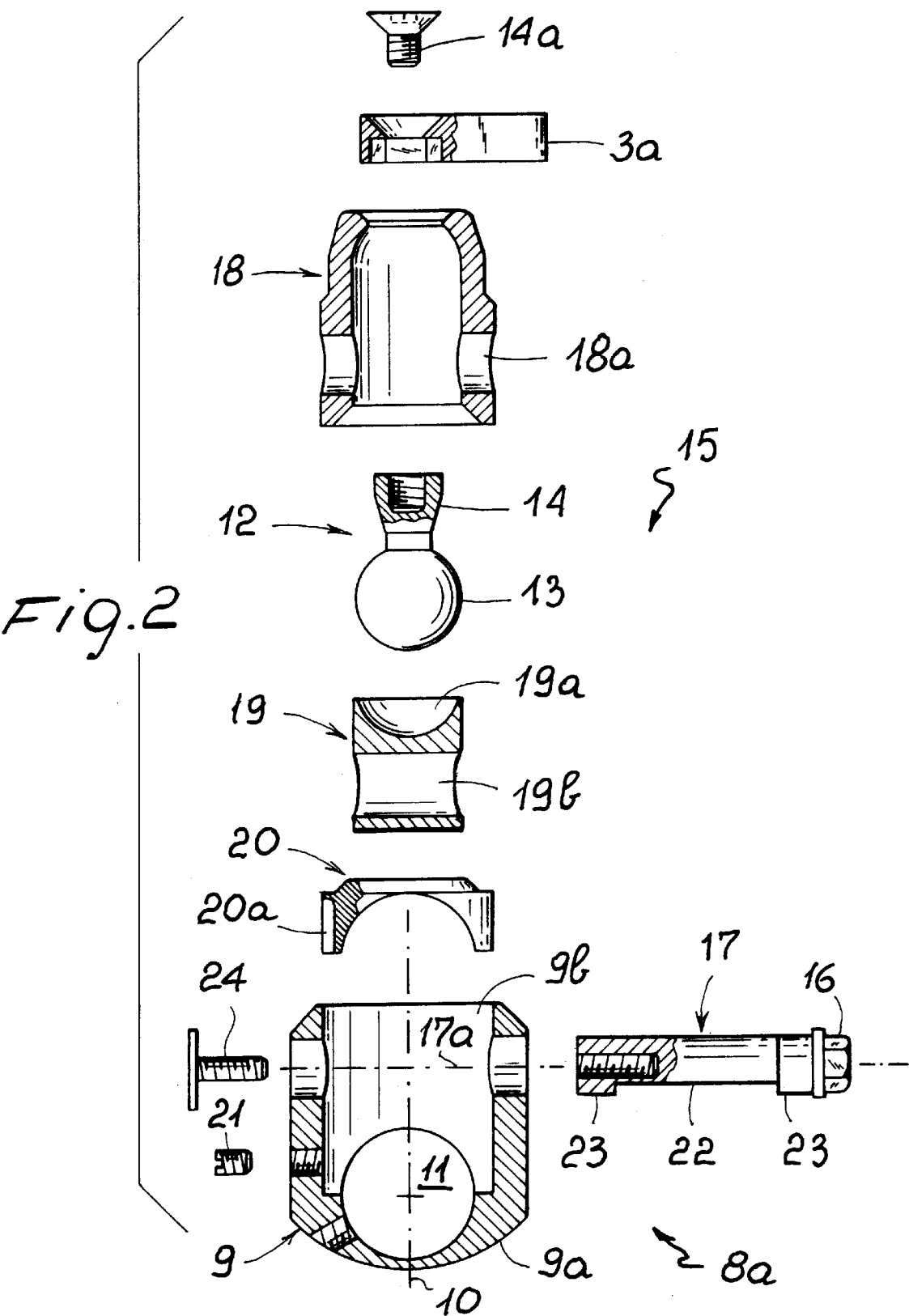
FIG. 2 is an exploded view in section of a portion of the fixing device at one said turret-like support.

With reference to the drawings, the fixing device in accordance with the invention is identified by reference numeral 1 and is shown in its preferred embodiment consisting of a single-sided outer fixing device for treatment of bone fractures, using surgical elements such as surgical screws.

Said screws are denoted by 2 and in FIG. 1 are for example tightened by groups through clamps 3 or similar devices, known per se. The fixing device 1 comprises a bar 4 having a longitudinal axis 6. Bar 4 has circular sections the center of which is on the longitudinal axis 5 and comprises a first and a second lengths 4a and 4b which are coaxial, tubular and mutually telescopic and rotating. The first length 4a is the one having the greater diameter and it incorporates the second length 4b of smaller diameter at least partly.

Bar lengths 4a and 4b are associated with stop contrivances 6 and 7 for stopping mutual translation and rotation, respectively.

Translation-stopping contrivances 6 comprise a side cap 6a to be screwed down to a free end of the first length 4a and a long threaded rod 6b internal to the first length 4a and to be screwed down to said first length and to the second length 4b. The rotation-stopping contrivances 7 comprise a screw to be inserted into the first length 4a in a direction transverse to the longitudinal axis 5, until engagement of the second length 4b. The screw can be associated with a runner or other device. Mounted on bar 4, on the first length 4a and second length 4b respectively, is a first and a second turret-like supports 8a and 8b, supporting the surgical screws 2, as pointed out hereinafter.

The first turret-like support 8a can be freely positioned relative to the first length 4a, and in fact it is movable in respect of the latter both coaxially and rotatably, irrespective of the mutual positions of lengths 4a, 4b.

The second turret-like support 8b can be either movable relative to the second length 4b, or fixed to an end of said second length. In fact, for its positioning it takes advantage of the mobility of the second length 4b relative to the first length 4a and the mobility of the first turret-like support 8a relative to the first length 4a. Each turret-like support comprises a glass-shaped outer casing 9 having an extension direction 10 passing through a substantially closed bottom 9a and an open mouth 9b. Bar 4 passes through the outer casing 9 at a hole 11 which is close to bottom 9a and directed transversely of the extension direction 10. An articulated joint 12 is placed at mouth 9b and it is angularly movable relative to the outer casing 9 and is adapted to provide the surgical screws 2—and generally the surgical elements mounted on the fixing device 1—with a large possibility of angular adjustment in position.

In fact the articulated joint 12 is a ball joint comprising a spherical body 13 integral with a tailpiece 14 projecting from the outer casing 9.

The surgical screws 2 and clamps 3 are in engagement with the tailpiece 14. FIG. 1 shows, by way of example, that clamps 3 are provided with adapter plates 3a capable of being fastened to tailpieces 14 by means of connecting screws 14a. Engagement means and relative drive means are provided for both the turret-like supports 8a, 8b or at least for the first support 8a movable on the first bar length 4a, for fixing position of the outer casing 9 on bar 4, and also engagement means and relative drive means are provided for fixing the angular position of the articulated joint 12.

All said engagement means are embodied, in particular for the first turret-like support 8a, by a single locking device 15. In addition, all said relative drive means are embodied by a single member 16 for the locking device 15.

The locking device 15 comprises a cam 17 supported by the outer casing 9 and extending between bar 4 and the articulated joint 12 and such movable that, when it is in a forcing position, forced pressing contacts are set up on bar 4 and the articulated joint 12.

In detail, cam 17 is rotating and engages a tie rod 18, better specified in the following, so that when the cam rotates from an inactive position to said pressing position, tie rod 18 is moved from a rest position, where the same is freely oscillating, to a work position, at which the articulated joint 12 and bar 4 are in a fixed position with respect to the turret-like support 8a.

In the embodiment shown, for obtaining simultaneous and identical sure locking actions, tie rod 18 acts in a direct manner only on the articulated joint 12, dragging the same along and forcing it towards bar 4 until both the articulated joint 12 and bar 4 are locked.

Tie rod 18 is of tubular form and partly incorporates the spherical body 13 at one end thereof, taking a substantially bell-shaped conformation on the whole. Then a counter-block 19 is provided between the spherical body 13 and bar 4 and it can be stressed to compression between them when the bell-shaped tie rod 18 drags along the spherical body 13 towards bar 4.

Counter-block 19 directly engages with the spherical body 13, and its shape matches that of said spherical body at an end cavity 19a, while it is in engagement with bar 4 upon interposition of a saddle-shaped coupling 20 conforming in shape to the bar itself.

Practically, when the bell-shaped tie rod 18 drags along the spherical body 13 towards bar 3, the counter-block 19 is compressed between the spherical body 13, on the one hand, and the saddle-shaped coupling 20 and bar 4, on the other hand.

The saddle-shaped coupling 20 is guided to its correct position by a guide dowel 21 to be inserted into a groove 21a. The guide dowel is necessary when turret 8a is mounted externally of bar 4.

Cam 17 is preferably embodied by a shaped pin rotating under the action of said drive member 16 around a rotation axis 17a. The rotation axis 17a of the cam or shaped pin 17 is transverse to the extension direction 10 of the outer casing 9 of the first turret-like support 8a. The cam or shaped pin 17 has a central eccentric portion 22 and ends 23 rotatably connected to the outer casing 9.

The eccentric portion 22 has circular sections clearly offset with respect to the rotation axis 17a and the bell-shaped tie rod 18 is in engagement with the eccentric portion 22 at annular holes 18a.

It is then to be noted that the eccentric portion 22 passes through the counterblock 19 with play, at a through hole 19b of wide sizes.

The technical solution hereabove described has the advantage that very precise sizes for the different members are not required and that the same locking for pivot 12 and bar 4 is assured.

In a different embodiment, the bell-shaped tie rod 18 may have such a length that in its work position it directly engages bar 4 too, through the saddle-shaped coupling 22. The bell-shaped tie rod 18 in this case must have an exactly gauged length, greater than that shown.

Figure 6:
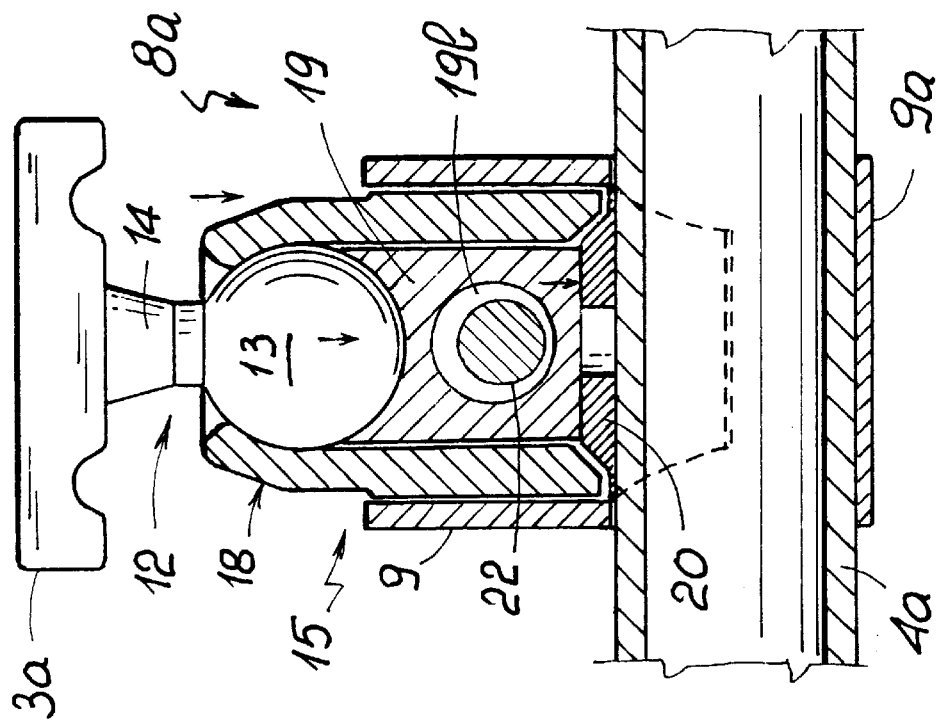
FIG. 6 is a section taken along line VI—VI in FIG. 5.
Figure 5:
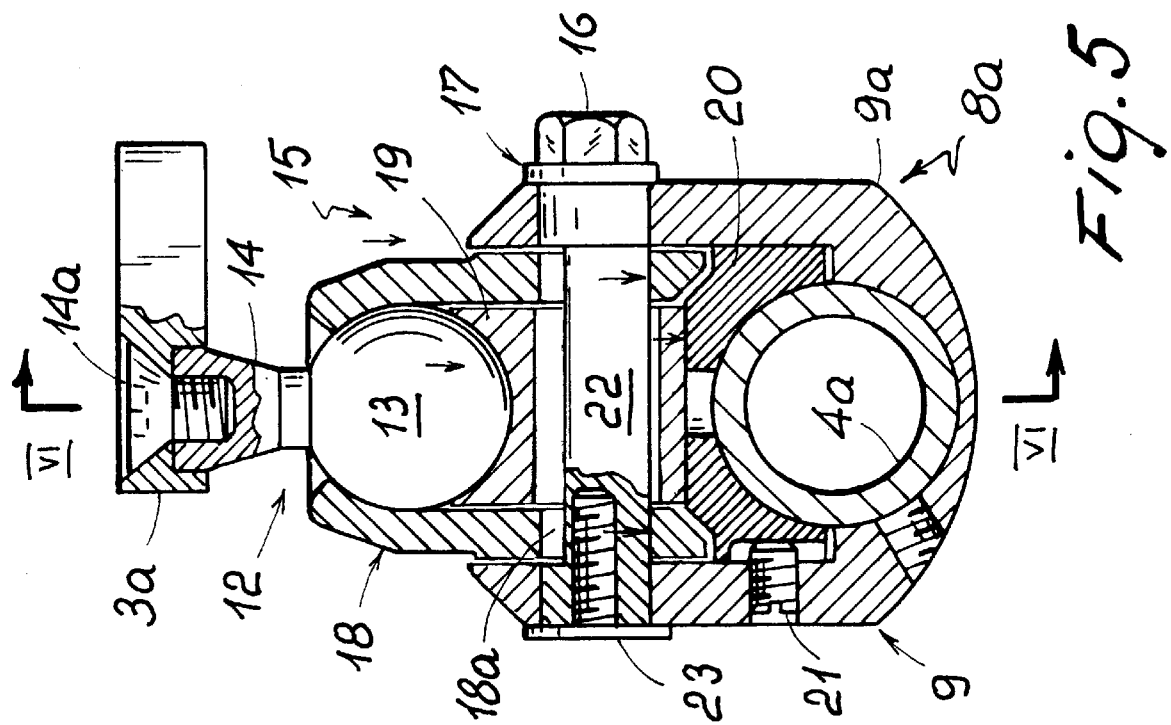
FIG. 5 shows the elements in FIG. 2 in a mounted position and in a tightened condition.

A further embodiment using the same elements but of demanding construction, may provide that cam 17 in the forcing position shown in FIGS. 5 and 6 should also engage counter-block 19, thereby pressing this counter-block too in addition to pressing tie rod 18.

In this instance, position of the through hole 19b must be very precise, as well as sizes of all elements, in order to avoid a weak locking of the articulated joint 12 and a strong locking of bar 4.

It will be also recognized that the drive member 16 is embodied by the head of the shaped pin 17 projecting from the outer casing 9 of the turret-like support and operable by a spanner. In fact it has the shape of a nut.

On the opposite side from the drive member 16, the shaped pin 17 is engaged by an axial set screw 24 making position of pin 17 steady relative to the outer casing 9.

Figure 7:
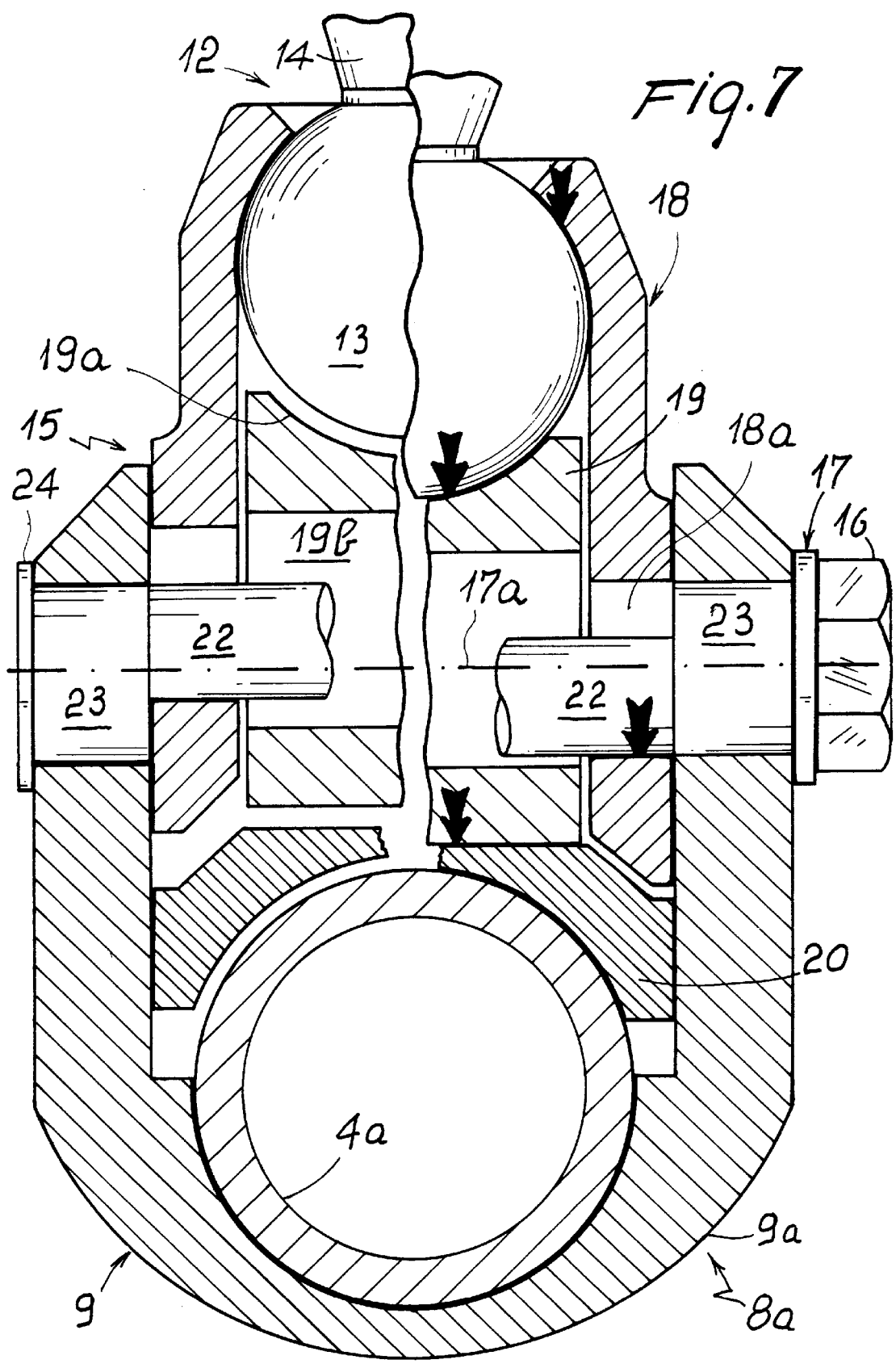
FIG. 7 highlights the different positions of the elements in FIGS. 3 and 5 by two partial sections disposed in side by side relationship.

Operation of the fixing device 1 is as follows, with particular reference to FIG. 7 showing two operating positions in side by side relationship.

The surgical elements or screws 2 must be arranged and applied in a manner known per se. Positions vary case by case depending on requirements and choices done.

The fixing device 1 is employed to keep the previously selected or reached positions steady and is capable of adapting itself to these positions. In fact, the fixing device 1 may accept any position of the surgical elements, due to the telescopic bar having lengths 4a, 4b to be freely positioned, to the possibility of movement of at least one turret-like support 8a on bar 4, and to the articulated joints 12 by which the surgical elements 2 are connected with the turret-like supports 8a, 8b.

Figure 4:
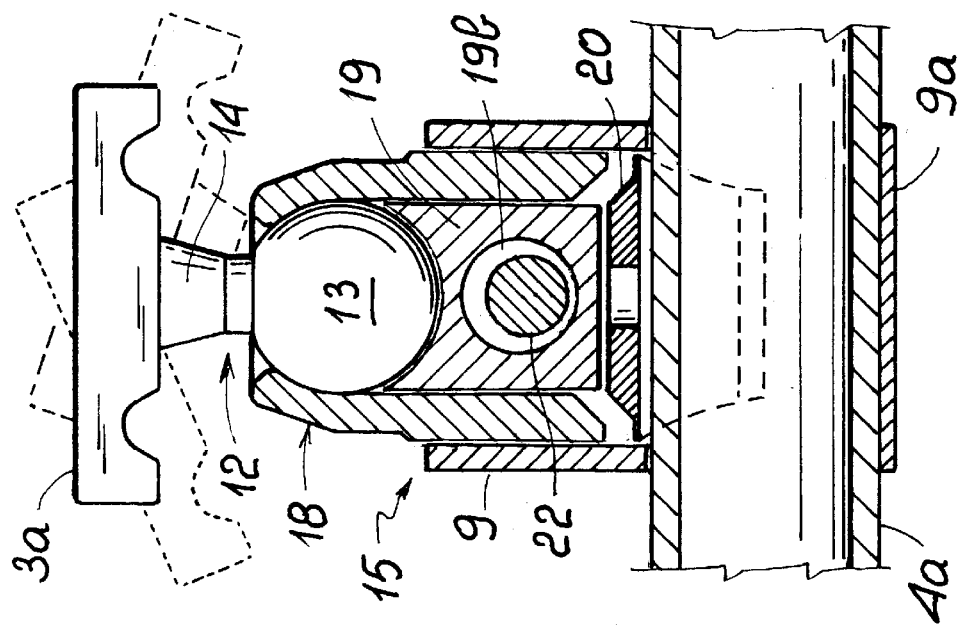
FIG. 4 is a section taken along line IV—IV in FIG. 3.
Figure 3:
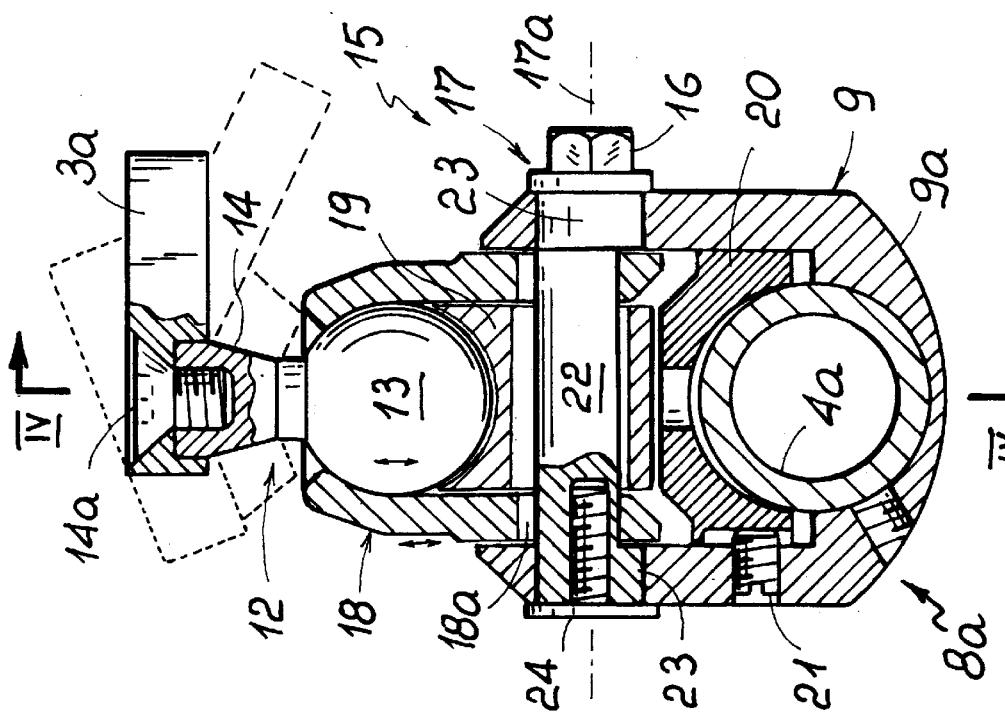
FIG. 3 shows the elements of FIG. 2 in a mounted position and in a freemovement condition.

This situation is highlighted in FIGS. 3 and 4 and on the left side of FIG. 7 where no forcing is applied to the spherical body 13 and to bar 4. When the optimal position has been identified, both fixing of lengths 4a, 4b through the stop contrivances 6 and 7 and locking of the turret-like supports and articulated joints with the aid of the locking device 15 can be executed In an immediate and reliable manner.

Said locking device is set in operation by the nut-shaped drive member 16 through a common spanner.

In fact, by rotating the drive member 16 around the rotation axis 17a, the shaped pin 17 passes from the preceding inactive position to the forcing position shown in FIGS. 5 and 6 and on the right side of FIG. 7. i.e. with the central eccentric portion 22 moved towards bar 4.

In this way the bell-shaped tie rod 18, in turn, passes from the preceding rest position to the work position, shifted towards bar 4, without on the other hand getting into contact with the latter or the saddle-shaped coupling 20. The bell-shaped tie rod 18 moves the spherical body 13 and the counter-block 19. Moving forward of counter-block 19 towards bar 4 is however stopped by the bar itself that, upon interposition of the saddle-shaped coupling 20, sets into forced contact with counter-block 19.

Under this situation block 19 is pressed between the articulated joint 12 and bar 4 and prevents them from moving. Locking is also automatically applied to the articulated joint and the bar, because they are aligned on the same kinematic chain.

Movement of counter-block 19 towards bar 4 is not hindered by its being passed through by the shaped pin 17 because crossing takes place at a through hole 19b of very large sizes, capable of avoiding interferences.

The invention achieves important advantages. In fact, a fixing device has been made in which the surgical elements are provided with different degrees of freedom or movement and positioning directions, so that all requirements can be met.

This result has been reached by adopting a simple and reliable technical solution that above all has the advantage of being lockable by means of a single and simple drive involving rotation of a spanner. Therefore the application time is greatly reduced.

In addition, tightening is completely reliable and error proof because the locking device 15 is capable of acting on the articulated joint and the bar simultaneously, with the same force and without any possibility of errors. In fact it is the articulated joint that is dragged along towards the bar to achieve locking of both of them.

What is claimed is:

1. An outer fixing device for orthopedics and traumatology comprising:
    a bar (4) having a longitudinal axis (5);
    at least one turret support (8a) having an outer casing (9) movably engagable on the bar (4);
    at least one articulated joint (12) for supporting surgical elements (2) moveably engagable to said outer casing (9);
    and fastening means for simultaneously fixing the outer casing (9) to the bar (4) and the articulated joint (12) to the outer casing (9) in a selected angular position;
    wherein said fastening means comprises;
    a locking device (15) having at least one cam (17) located between the bar (4) and the articulated joint (12);
    and a drive member for rotating the cam (17) to a position where the cam fixedly engages the outer casing (9) to the bar (4) and the articulated joint (12) to the outer casing (9) in the angular position selected.

2. A fixing device as claimed in claim 1 wherein said locking device (15) comprises a tie rod (18) extending between said cam (17) and said articulated joint (12), said tie rod (18) being moveable by said cam (17) between a rest position, at which said articulated joint (12) can be movably adjusted and a work position, at which said articulated joint (12) is held in a fixed position by said tie rod (18).

3. A fixing device as claimed in claim 2, wherein said articulated joint (12) comprises a spherical body (13) and wherein said tie rod (18) is of tubular configuration and partly incorporates said spherical body (13).

4. A fixing device as claimed in claim 2, wherein said locking device (15) comprises a counter-block (19) inserted between said articulated joint (12) and the bar (4), and wherein said tie rod (18) is movable along said articulated joint (12) towards said bar (4) until said counter-block (19) is compressed to fix said articulated joint (12) and the bar (4) together.

5. A fixing device as claimed in claim 4, wherein said counter-block (19) has a shape corresponding to that of said articulated joint (12) and can be directly engaged by said joint, and wherein a saddle coupling (20) corresponding in shape to that of said bar (4) is inserted between said counter-block (19) and the bar (4).

6. A fixing device as claimed in claim 4, wherein said cam (17) is a shaped rotating pin having a rotation axis (17a) and passes through said counter-block (19) with play, and wherein said shaped pin has ends (23) coaxial with said rotation axis (17a) and rotatably supported by said outer casing (9), and at least one eccentric portion (22) placed between said ends (23) to engage said tie rod (18).

7. A fixing device as claimed in claim 6, wherein said eccentric portion (22) has, perpendicularly to said rotation axis (17a), a circular section offset relative to said rotation axis (17a).

8. A fixing device as claimed in claim 1, wherein said cam (17) is a shaped pin rotatably supported by said outer casing (9) and wherein said drive member (16) is a head of said shaped pin projecting from said outer casing (9) which can be actuated by a spanner.

9. A fixing device as claimed in claim 1, wherein said outer casing (9) is glass shaped and has a bottom (9a), an open mouth (9b) and an extension direction (10) passing through said bottom (9a) and the open mouth (9b), Wherein said bar (4) passes through said outer casing (9) at said bottom (9a), and wherein said articulated joint (12) is located at said open mouth (9b).

10. A fixing device as claimed in claim 1, wherein said bar (4) has circular sections and comprises a first and a second length (4a, 4b) coaxial and telescopic with each other and mutually rotating, and stop contrivances for respectively stopping translation and rotation (6, 7) between said first and second bar length (4a, 4b).

11. A fixing device as claimed in claim 1, wherein said turret support (8a) is movable coaxially of said bar (4) and is rotatable about said longitudinal axis (5), in the absence of locking.

12. A fixing device as claimed in claim 10, wherein provision is made for said at least one turret support (8a) to be adjustably positioned relative to said first length (4a) of said bar (4) and a second turret support (8b) fixed to said second length (4b), at an end of said bar (4).

* * * * *